United States Patent [19]

Levy

[11] Patent Number: 4,976,354

[45] Date of Patent: Dec. 11, 1990

[54] CARRIER PACKAGE FOR BIOLOGICAL SPECIMAN SLIDE

[76] Inventor: Abner Levy, 325 N. Oakhurst Dr., #4, Beverly Hills, Calif. 90210

[21] Appl. No.: 491,878

[22] Filed: Mar. 12, 1990

[51] Int. Cl.$^5$ .................... B65D 85/48; B65D 73/00
[52] U.S. Cl. ................................. 206/456; 206/476; 206/474; 206/482
[58] Field of Search .............. 206/456, 455, 472, 473, 206/474, 482

[56] References Cited

U.S. PATENT DOCUMENTS

| D. 138,698 | 9/1944 | Salfisberg | 206/472 X |
| 2,198,138 | 4/1940 | Sutton | 206/482 |
| 3,141,547 | 7/1964 | Newby | 206/456 X |
| 3,141,548 | 7/1964 | Newby | 206/456 X |
| 4,078,656 | 3/1978 | Crane et al. | 206/456 X |

*Primary Examiner*—William I. Price

*Attorney, Agent, or Firm*—Natan Epstein

[57] ABSTRACT

A package for biological specimen slides made of an elongated sheet divided by a transverse crease line into a cover portion and a base portion. A tab at one end engages a slot near the opposite end for keeping the sheet folded along the crease line to cover a slide held between the base and cover by two slide retainers on the base portion. The cover is longer than the base and arches away from contact with a biological specimen on the slide. One slide retainer has a retaining strip defined between two openings in the base for holding one end of the slide inserted under the retaining strip and bridging the two openings. The second slide retainer has an opening defined in part by two oblique edges and a tab extending into the opening between the oblique edges, such that the opposite end of the slide can be inserted into the opening and engaged between the oblique edges and the tab.

18 Claims, 1 Drawing Sheet

U.S. Patent     Dec. 11, 1990     4,976,354
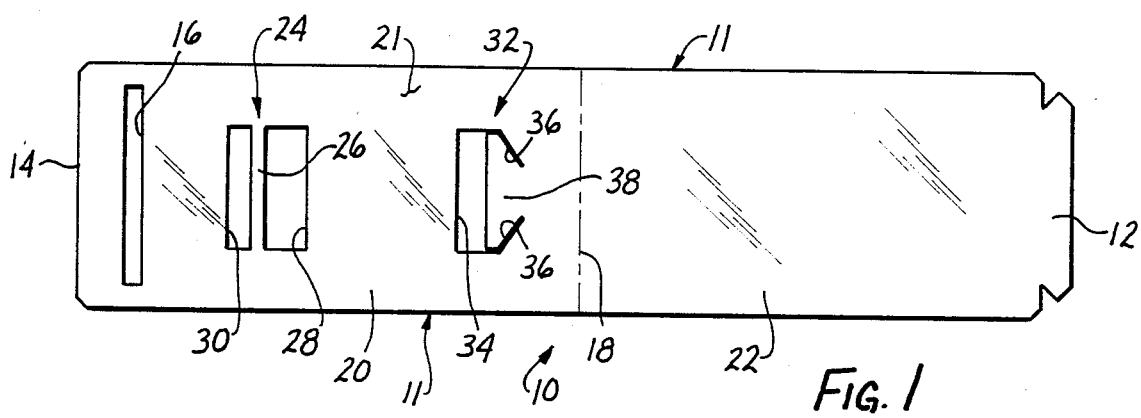
FIG. 1
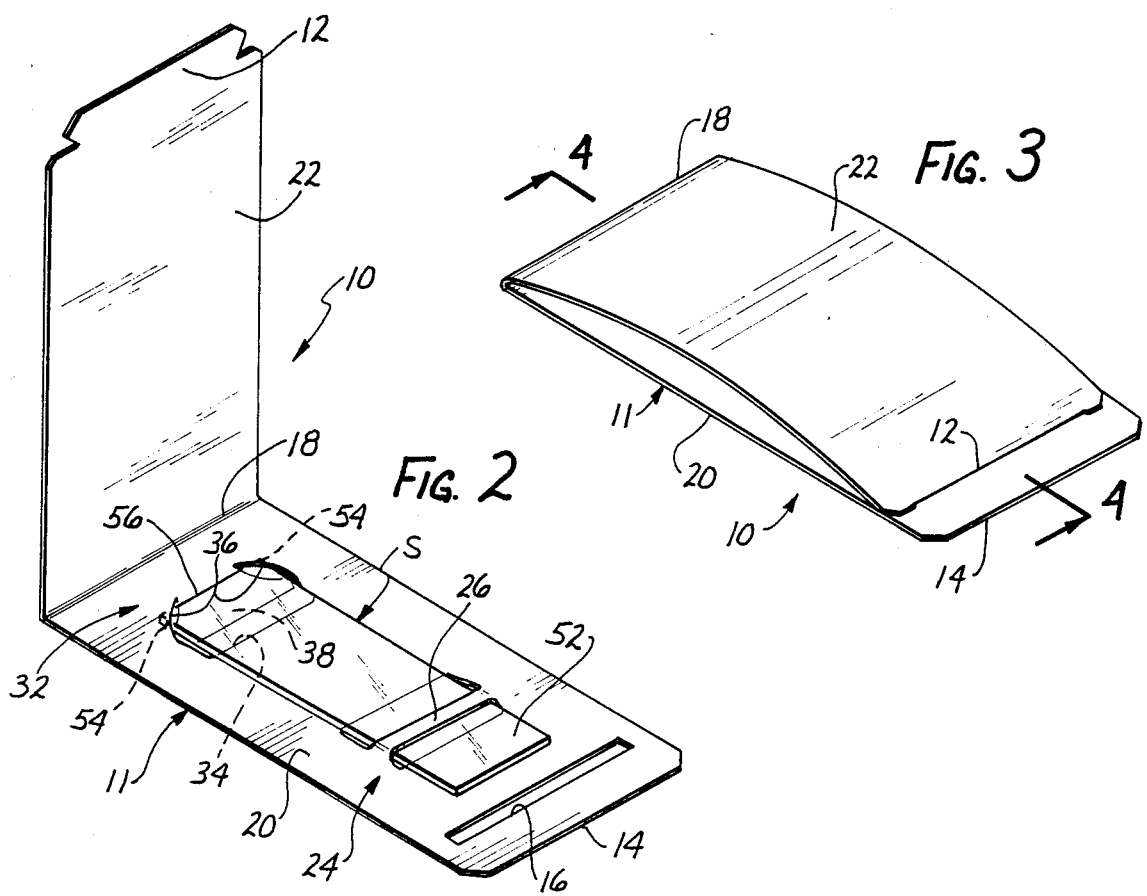
FIG. 2
FIG. 3
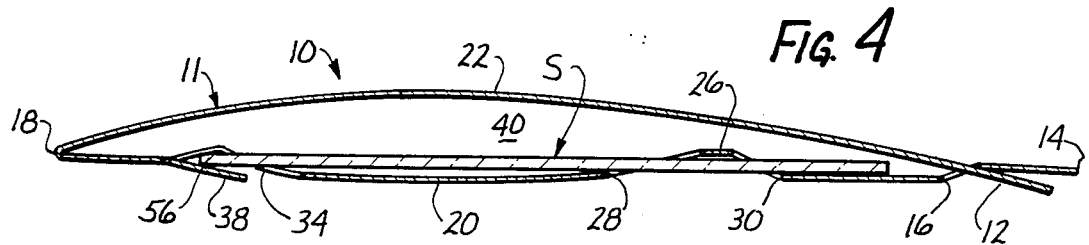
FIG. 4

CARRIER PACKAGE FOR BIOLOGICAL SPECIMAN SLIDE

BACKGROUND OF THE INVENTION

FIELD OF THE INVENTION

It is current medical practice in the screening of patients for various medical disorders to collect small specimens of tissue, scrapings or fluid for subsequent laboratory analysis. These specimens are collected by means of small tools suited for this purpose and deposited on a specimen carrier which typically is a glass slide suitable for viewing of the specimen under a microscope, or for testing of the specimen with chemical reagents.

It is usual for these specimen slides to be placed within a protective package immediately upon collection so as to protect the specimen during subsequent handling and transport to the laboratory. Such packages are made of lightweight pliable stock such as heavy paper or light cardboard. A single sheet is cut with various tabs, flaps, openings etc., in different configurations.

The collection of biological samples for analysis is frequently, carried out under time pressure and less than ideal working conditions. Also, current practice is to wear protective gloves while collecting medical specimens as a precautionary measure against contagion, which adds to the difficulty of quickly and properly handling the small glass specimen slide, placing it into its protective package without smearing the specimen which is exposed on the glass surface, and then folding closed the package.

Since, the specimen package is discarded at the laboratory, it is desirable for such packages to be low cost, while at the same time being very simple in construction, easy to use, and reliable in protecting the slide and the specimen. A continuing need exists for greater simplicity of manufacture, ease of use and improved package performance.

SUMMARY OF THE INVENTION

The specimen package of this invnetion addresses the aforementioned needs and objective by providing a package for holding and carrying a biological specimen slide, which package is made of an elongated sheet of foldable stock, such as paper or cardboard, having two opposite ends and divided between the ends by a transverse crease line into a cover portion and a base portion. Retaining elements at or near each end are mutually engageable for fastening the ends together to hold the sheet folded along the crease line. Th slide is carried on the base portion by two slide retainers arranged on the base portion between the crease line and one of the sheet ends for holding the slide between the two portions of the folded sheet.

The cover portion arches away from contact with a slide retained in said carrier means to protect a biological specimen deposited on the slide. This arching is obtained because the cover portion is longer than the base portion between the crease line and the corresponding retaining elements such that the cover portion is forced into an arcuate configuration upon engagement of the retaining elements. The retaining elements may be, for example, a tab at one end of the package and a slit near the opposite end. By engaging the tab in the slit the two ends are held together, keeping the package folded closed.

The first slide retainer has a transverse retaining strip defined between two openings in the base portion such that one end of the slide inserted under the retaining strip and bridging the two openings is retained against the base portion.

The second slide retainer engageable with the opposite end of the slide is adapted to stop longitudinal sliding of the slide at least in one direction under the retaining strip of the first retainer. In particularly, the second retainer includes an opening defined in part by two oblique edges and a tab extending into the opening between the oblique edges, such that the opposite end of the slide can be inserted into the opening and is engaged between the oblique edges and the tab.

These and other features and advantages of this invention will be better understood from the following detailed description with reference to the attached drawings.

BRIEF DESCRIPTION OF THE DRAWINGS

FIG. 1 is a plan view of the specimen package of this invention shown laid flat in its unfolded condition;

FIG. 2 is a perspective of the package of FIG. 1 showing a specimen slide retained in the package and the cover folded at a right angle relative to the base portion of the package;

FIG. 3 shows the package of FIG. 1 with the cover closed and secured to the base portion of the package ready for handling and transport to a laboratory;

FIG. 4 is a longitudinal section taken along line 4—4 in FIG. 3 illustrating the engagement of the specimen slide in the package.

DETAILED DESCRIPTION OF THE PREFERRED EMBODIMENTS

Turning to FIG. 1, a specimen package designated by the numeral 10 is seen to consist of a single elongated, generally rectangular sheet of pliable stock such as lightweight cardboard. The package sheet 11 has two parallel side edges 13 and two opposite ends: a first end at which is defined an end tab 12 and an opposite end 14 near which is cut a transverse slot 16 sized to receive the end tab 12. Between these two ends, the sheet 10 is divided by a transverse crease line 18 into a base portion 20 and a cover portion 22. The sheet 10 is intended to fold along the crease line 18, as shown in FIG. 2 where the cover portion 22 is folded to a right angle relative to the base portion 20. In FIG. 3, the package is shown fully closed with the cover 22 folded over the base 20, and the retaining tab 12 engaged in the tab receiving slot 16 thereby securing together the two ends of the sheet 10.

The base 20 is adapted to carry and retain a specimen slide S shown in FIGS. 2 and 4. The slide S is an elongated rectangular slide of thin glass or plastic on which the physician or medical technician deposits a smear of the material to be examined or analyzed. The slides usually employed for this purpose have, at one end, an especially treated area 52 on which identifying marks or information may be written, to identify the specimen as pertaining to a particular patient. It is thus important that the slide identification area 52 be visible while the slide is retained in the package 10. Two separate slide retainers are provided for carrying the slide S on the base portion 20. A first slide retainer generally designated by numeral 24 includes a thin transverse strip 26 defined between two openings, an inner opening 28 and an outer opening 30. These two openings are rectangular windows cut in the sheet stock and slightly spaced apart to define the narrow strip 26. The width of the openings, and the length of the strip, is only slightly greater than the width of the slide to be retained to substantially keep the slide againsts significant lateral displacement on the base 20. The slide S is engaged to the retainer 24 by slipping one end of the slide first into the smaller outer opening 30, then under the retaining strip 26 and finally back up through the larger, inner opening 28. The slide is in effect threaded under the retaining strip 26 and then pushed along the base 20 until it bridges both openings 28 and 30 and the strip 26 holds the slide down against the inside surface 21 of the base 20. This condition of the slide is shown in FIGS. 2 and 4. The identification area 52 will normally lie on the outside of the retaining strip 26 i.e. over a portion of the base 20 lying between the strip 26 and the tab receiving slot 16. The information written on this area remains plainly and easily visible upon lifting the cover 22 away from the base 20. Further, underlying portion of the base 20 which will typically be white or light colored, provides a clean high contrast background for easy and clear legibility of the markings on the slide area 52.

The slide S is capable of sliding movement under the retaining band 26 of the first retainer 24 along the longitudinal dimension of the package 10. In order to better secure the slide S, the opposite end 56 is engaged to a second retainer generally designated by numeral 32 and which includes an opening 34 defined in part by two oblique sides 36. These two sides are segments cut at approximately a 45 degree angle to the transverse crease line 18, as well as to the side edges of the package 10. The oblique sides 36 point towards the end tab 12 but stop short of intersecting each other, as shown in FIG. 1. A tab 38 connected to the base portion 20 between the two oblique cuts 36 extends into the opening 34. The tab 38 can be bent up or down along an imaginary line connecting the ends of the oblique segments 36. Preferably, the width of the opening 34 at its widest end is equal to the width of the openings 28, 30 of the first retainer so as to hold the slide against lateral movement relative to the base 20.

The end of the slide S opposite to the one retained by the first retainer 24 is engaged to the second retainer 32 as shown in FIG. 2. The corners 54 of the slide end 56 are slipped under the oblique edges 36 while pressing the tab 38 under the slide S. This condition is best appreciated by reference to the cross section of FIG. 4. The inherent resilience of downwardly deflected tab 38 tending to return to its original coplanar relationship with the base portion 20 urges the slide end 56 upwardly, and the corners 54 up against the underside of the base adjacent to the oblique edges 36. In effect the result is a gripping effect on the slide end 56 which tends to hold the slide against movement relative to the retaining strip 26. At the very least, the second retainer 32 serves as a positive stop against sliding movement of the slide S towards the end tab 12. The gripping effect of this retainer will also tend to hold the single against movement in the opposite direction.

The slide S is mounted to the package 10 by first engaging to the first retainer 24 as described above, then pressing the end 56 into the opening 34 to push down the tab 38 of the second retainer, and pushing the slide a short distance towards the crease line 18 into a press fit against the tab 38 as the slide corners 54 are caught under the oblique edges 36.

An important feature of the package 10 of the invention is the fact that in the fully closed condition of FIG. 3, with the end tab 12 engaged to the tab receiving slot 16, the cover portion 22 arches over the base 20 away from contact with the slide S. This arching is obtained by virtue of a difference in length between the cover and base as measured between the crease line 18 and the corresponding end-retaining elements i.e. the tab 12 and slot 16. Specifically, the length of the cover 22 measured between the crease line 18 and the tab 12 is somewhat greater than the length of the base portion 20 as measured between the crease line 18 and the tab receiving slot 16. Consequently, when the tab 12 is inserted into and retained in the slot 16, the cover 22 is forced to flex and arch along its intermediate portion away from the base 20. FIG. 4 shows the dome-like inner space 40 defined by the arched cover 22 over the slide S. The curved cover 22 offers significant resistance to flattening under moderate downward pressure, because both ends of the cover are secured to the base, one along the common crease line 18, the other by means of the tab 12 and, under pressures typically encountered during proper handling of such packages by trained personnel, the cover 22 will resist pressure and maintain spacing from the exposed upper surface of the slide S, thereby preserving the biological specimen on the slide surface. In the closed condition of FIGS. 3 and 4, the packages 10 can therefore tolerate normal handling during transport while protecting the specimen slide.

From the foregoing, it will be appreciated that the package 10 of this invention is of considerable simplicity in that it is made up of a single sheet divided only into a base portion and a cover portion, as compared to previous packages of this nature featuring multiple slide flaps, complex slit lines, perforation lines, tabs and openings. Thus, this package can be comfortably and securely held in one hand while the slide is easily inserted with the other.

While a preferred embodiment of the invention has been described and illustrated for purposes of clarity and example, it must be understood that many changes, substitutions and modifications to the described embodiment will become readily apparent to those possessed of ordinary skill in the art, and that such modifications remain within the scope of this patent as defined by the following claims.

What is claimed is:

1. A package for a biological specimen slide, comprising:
    an elongated sheet of foldable stock having two opposite ends and divided between said ends by a transverse crease line into a cover portion and a base portion;
    retaining means engageable for fastening said ends together with said sheet folded along said crease line;
    carrier means on said base portion between said crease line and said ends for retaining a slide between said portions of said folded sheet;
    characterized in that said cover portion arches away from contact with a slide retained in said carrier means to protect a biological specimen deposited on the slide.

2. The package of claim 1 wherein said cover portion is longer than said base portion between said crease line and said retaining means such that said cover portion is forced into an arcuate configuration by engagement of said retaining means.

3. The package of claim 1 wherein said carrier means includes a first slide retainer comprising a transverse retaining strip defined between two openings in said base portion such that one end of the slide inserted under said retaining strip and bridging said openings is retained against said base portion.

4. The package of claim 3 wherein said carrier means further includes a second slide retainer engageable with the opposite end of the slide.

5. The package of claim 4 wherein said second slide retainer is adapted to stop sliding of said slide at least in one direction under said retaining strip.

6. The package of claim 4 wherein said second retainer means includes an aperture defined in part by two oblique edges and a tab between said oblique edges such that the opposite end of the slide can be inserted into said aperture and retained between said oblique edges and said tab.

7. A package for a biological specimen slide, comprising:
an elongated sheet of foldable stock having two opposite ends and divided between said ends by a transverse crease line into a cover portion and a base portion;
means for retaining said ends together with said sheet folded along said crease line;
carrier means on said base portion between said crease line and said ends for retaining a slide between said portions of said folded sheet;
said carrier means including a first slide retainer comprising a transverse retaining strip defined between two openings in said base portion such that one end of the slide inserted under said retaining strip and bridging said openings is retained against said base portion.

8. The package of claim 7 wherein said carrier means further includes a second slide retainer engageable with the opposite end of the slide.

9. The package of claim 8 wherein said second slide retainer is adapted to stop sliding of said slide at least in one direction under said retaining strip.

10. The package of claim 8 wherein said second retainer means includes an aperture defined in part by two oblique edges and a tab between said oblique edges such that the opposite end of said slide can be inserted into said aperture and retained between said oblique edges and said tab.

11. A package for a biological specimen slide, comprising:
an elongated sheet of foldable stock having two opposite ends and divided between said ends by a transverse crease line into a cover portion and a base portion;
means for retaining said ends together with said sheet folded along said crease line;
carrier means on said base portion between said crease line and said ends for retaining a slide between said portions of said folded sheet;
characterized in that said cover portion arches away from contact with a slide retained in said carrier means to protect a biological specimen deposited on the slide; and
wherein said carrier means includes a first slide retainer comprising a transverse retaining strip defined between two openings in said base portion such that one end of the slide inserted under said retaining strip and bridging said openings is retained against said base portion.

12. The package of claim 11 wherein said carrier means further includes a second slide retainer engageable with the opposite end of the slide.

13. The package of claim 12 wherein said second slide retainer is adapted to stop sliding of said slide at least in one direction under said strip.

14. The package of claim 12 wherein said second retainer means includes an aperture defined in part by two oblique edges and a tab between said oblique edges such that the opposite end of the slide can be inserted into said aperture and retained between said oblique edges and said tab.

15. The package of claim 11 wherein said cover portion is longer than said base portion between said crease line and said retaining means such that said cover portion is forced into an arcuate configuration by engagement of said retaining means.

16. A package for a biological specimen slide, comprising:
an elongated sheet of a foldable stock having two opposite ends and divided between said ends by a transverse crease line into a cover portion and a base portion;
means for retaining said ends together with said sheet folded along said crease line;
a first slide retainer comprising a transverse retaining strip defined between two openings in said base portion such that one end of the slide inserted under said retaining strip and bridging said opening is retained against said base portion;
a second slide retainer includes an aperture defined in part by two oblique edges and a tab between said oblique edges such that the opposite end of the slide can be inserted into said aperture and retained between said oblique edges and said tab; and
wherein said cover portion is longer than said base portion between said crease line and said retaining means such that said cover portion is forced into an arcuate configuration away from said base portion by engagement of said retaining means thereby to avoid contact with a slide on said base portion.

17. A package for a biological specimen slide, comprising:
a base sheet including retaining means for holding a specimen carrier on said base sheet;
a cover sheet releasably secured at opposite ends to said base sheet for covering a carrier held thereon; and
said cover sheet being longer than said base sheet between said ends such that said cover sheet arches away from contact with the carrier between the two ends.

18. The package of claim 17 wherein said base sheet and said cover sheet are joined along a crease line

* * * * *